US008486627B2

(12) United States Patent
Ma

(10) Patent No.: US 8,486,627 B2
(45) Date of Patent: Jul. 16, 2013

(54) METHODS, COMPOSITIONS, AND KITS FOR AMPLIFYING AND SEQUENCING POLYNUCLEOTIDES

(75) Inventor: Peter Nien-Tung Ma, Cupertino, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 180 days.

(21) Appl. No.: 12/684,089

(22) Filed: Jan. 7, 2010

(65) Prior Publication Data

US 2011/0070580 A1    Mar. 24, 2011

Related U.S. Application Data

(63) Continuation of application No. 11/044,236, filed on Jan. 26, 2005, now abandoned.

(60) Provisional application No. 60/539,465, filed on Jan. 26, 2004.

(51) Int. Cl.
*C12Q 1/68* (2006.01)

(52) U.S. Cl.
USPC .......................................................... 435/6.1

(58) Field of Classification Search
None
See application file for complete search history.

(56) References Cited

U.S. PATENT DOCUMENTS

| 5,210,412 | A | | 5/1993 | Levis et al. |
| 5,314,809 | A | | 5/1994 | Erlich et al. |
| 5,332,666 | A | | 7/1994 | Prober et al. |
| 5,518,900 | A | | 5/1996 | Nikiforov et al. |
| 5,789,168 | A | | 8/1998 | Leushner et al. |
| 5,800,996 | A | | 9/1998 | Lee et al. |
| 5,821,058 | A | | 10/1998 | Smith et al. |
| 5,863,727 | A | | 1/1999 | Lee et al. |
| 5,928,906 | A | | 7/1999 | Koster et al. |
| 5,945,526 | A | | 8/1999 | Lee et al. |
| 5,994,058 | A | * | 11/1999 | Senapathy .................... 435/6.18 |
| 6,124,094 | A | * | 9/2000 | Lajoie et al. ................. 435/6.18 |
| 6,225,450 | B1 | | 5/2001 | Koster |
| 6,280,949 | B1 | * | 8/2001 | Lizardi ........................ 435/6.18 |

FOREIGN PATENT DOCUMENTS

| EP | 1055736 | 11/2000 |
| WO | WO-89/07149 | 8/1989 |
| WO | WO-98/21361 | 5/1998 |
| WO | WO-99/37808 | 7/1999 |
| WO | WO-02/34883 | 5/2002 |
| WO | WO 0234883 A2 * | 5/2002 |
| WO | WO-03/056030 | 7/2003 |

OTHER PUBLICATIONS

International Search Report—PCT/US2005/002434 Jan. 2, 2006.
International Searching Authority Written Opinion PCT/US2005/002434 Jan. 2, 2006.
Birkenmeyer, et al., "Virological Methods", 1991, 117-126, 35.
Brenner, et al., "Gene Expression analysis by massively parallel signature sequencing (MPSS) on microbead arrays", *Nat Biotechnol.* Erratun (Nat Biotechnol Oct. 2000; 18(10):1201). Jun. 2000, 18(6):630-4.
Landegren, et al., "Trends Genetics", 1993, 199-202, 9.
Leamon, et al., "A Massive Parallel PicoTiterPlate Based Platform for Discrete Picoliter-Scale Polymerase Chain Reactions", *Electrophoresis.* Erratum in: Electrophoresis, Apr. 2004;25 (7-8):1176 Nov. 24, 2003, (21):3769-77.
Lizardi, et al., "Mutation Detection and Single-Molecule Counting Using Isothermal Rolling-Circle Amplification", *Nat Genet* Jul. 1998, 19(3):225-32.
Mitra, et al., "Fluorescent in Situ Sequencing on Polymerase Colonies", *Anal Biochem* Erratum in: Anal Biochem, May 15, 2004; 328(2):245 and Erratum in: Anal Biochem, 2004; 328:245. Sep. 1, 2003, 320(1):55-65.
Mucke, et al., "DNA Clevage by Type III Restriction-Modification Enzyme EcoP 15I is Independent of Spacer Distance Between Two Head to Head Oriented Recognition Sites", *J Mol Biol* Sep. 28, 2001, 312(4):687-98.
Nakano, et al., "Single-Molecule PCR Using Water-in-Oil Emulsion", *J Biotechnol* Apr. 24, 2003, 102(2):117-24.
Prober, et al., "A system for rapid DNA sequencing with fluorescent chain-terminanting dideoxynucleotides", *Science* Oct. 16, 1987, 238(4825):336:41.
Rao, et al., "Direct Sequencing of Polymerase Chain Reaction-Amplified DNA", *Analytical Biochemistry, Academic Press.* San Diego, CA, US Jan. 1994, 1-14, 216(1).
Ronaghi, et al., "Real-time DNA Sequencing Using Detection of Pyrophosphate Release", *Anal Biochem* Nov. 1, 1996, 242(1):84-9.
Ruano, G et al., "Genotyping and Haplotyping of Polymorphisms Directly from Genomic DNA Via Coupled Amplification and Sequencing (CAS)", *Nucleid Acids Rsearch, Oxford University Press* 1991, 6877-6882, 19(24).
Sanger, et al., "DNA Sequencing with Chain-Terminating Inhibitors", *Proc. Natl. Acad. Sci. USA* vol. 74, No. 12 1977, 5463-5467.
Sanger, et al., "Nucleotide Sequence of Bacteriophage Phi X174 DNA", *Nature* 265(5596) Feb. 24, 1997, 687-695.
Shendure, et al., "Advance Sequencing Technologies: Methods and Goals", *Nat Rev Genet.* May 2004; 5(5): May 2004, 335-344.
Tawfik, et al., "Man-Made Cell-Like Compartments for Molecular Evolution", *Nat Biotechnol* Jul. 1998, 652-656.

* cited by examiner

*Primary Examiner* — Christopher M. Babic

(57) ABSTRACT

In one aspect, there are provided methods of amplifying and sequencing a polynucleotide. In some embodiments, the method includes (a) amplifying the polynucleotide with at least one amplification primer, a processive amplification polymerase, a sequencing primer, a sequencing polymerase, deoxynucleoside triphosphates suitable for template-dependent primer extension, and one or more terminating nucleotides, the incubation being carried out at a first temperature suitable for amplifying the polynucleotide with the processive amplification polymerase; (b) incubating the product of step (a) at a second temperature suitable for forming a plurality of differently-sized extended sequencing primers with the sequencing polymerase; (c) evaluating the extended sequencing primers in order to determine the sequence of the polynucleotide. The reactions at the first and second temperatures can be carried out in a single reaction vessel. In other aspects, compositions and kits for carrying out the methods are also provided.

25 Claims, 3 Drawing Sheets

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: Phosphorothioate interlinkage
<220> FEATURE:
<221> NAME/KEY: misc_feature
<222> LOCATION: (17)..(18)
<223> OTHER INFORMATION: Phosphorothioate interlinkage
<220> FEATURE:
<223> OTHER INFORMATION: Description of Artificial Sequence: Synthetic
      primer

<400> SEQUENCE: 1
tgtaaaacga cggccagt                                                 18

<210> SEQ ID NO 2
<211> LENGTH: 18
<212> TYPE: DNA
<213> ORGANISM: Artificial Sequence
<220> FEATURE:
<221> NAME/KEY: misc_feature
<222> LOCATION: (16)..(17)
<223> OTHER INFORMATION: Phosphorothioate interlinkage
<220> FEATURE:
<221> NAME/KEY: misc_feature
<222> LOCATION: (17)..(18)
<223> OTHER INFORMATION: Phosphorothioate interlinkage
<220> FEATURE:
<223> OTHER INFORMATION: Description of Artificial Sequence: Synthetic
      primer

<400> SEQUENCE: 2
caggaaacag ctatgacc                                                 18

<210> SEQ ID NO 3
<211> LENGTH: 745
<212> TYPE: DNA
<213> ORGANISM: Unknown Organism
<220> FEATURE:
<223> OTHER INFORMATION: Description of Unknown Organism: Illustrative
      sequence data
<220> FEATURE:
<221> NAME/KEY: modified_base
<222> LOCATION: (2)
<223> OTHER INFORMATION: variable or unknown nucleotide
```

```
<220> FEATURE:
<221> NAME/KEY: modified_base
<222> LOCATION: (9)
<223> OTHER INFORMATION: variable or unknown nucleotide
<220> FEATURE:
<221> NAME/KEY: modified_base
<222> LOCATION: (16)
<223> OTHER INFORMATION: variable or unknown nucleotide
<220> FEATURE:
<221> NAME/KEY: modified_base
<222> LOCATION: (20)
<223> OTHER INFORMATION: variable or unknown nucleotide
<220> FEATURE:
<221> NAME/KEY: modified_base
<222> LOCATION: (688)
<223> OTHER INFORMATION: variable or unknown nucleotide

<400> SEQUENCE: 3
gntaggcgnt ctgagnctgn gttgacgtct tcgctgccga cagagattca ccgacagaat     60
tctgcggcgg tccatgttgt aggcggtgta gtccgtctgc gcaccacggg tggtctggga    120
accactaccc atcgcaatac tgtttgcatg atttgcactc gcgttgctac cgatagcaat    180
accgttgatt gcatcagtta acaccagagt gttcaggcca ataccgatcc ctgcatcacc    240
attaacaatg gttttcgcac ccattgccag cgagtcttca ccgacagcca gtgaatcttc    300
ttccgttgaa ttagcatgga agtatttgga cggtgtcgtt gctacagcac caatcgcatt    360
ctgcaattga cgaaccgtaa cggcgtcatg ggcttcggaa ccatcggcta cgttgatgat    420
ttgacgatat ttaccgtcat caccgataga caatgcaccg agcagttcgc catccgtggt    480
gtcgtaacca ataacaacgc catttttccgt tatgctggtg tcacgggagc ctttggcaat    540
cactcggctg gaaacagagc tgctacccag ggcgatatcc gtatcaacgt cgctgtagct    600
gccctgacca atagctacgc tgctatcgcc tttggcgaca gagttataac ctatagctgt    660
agcgccaaca ccctgtgcgc tggcgcgntt gaacgctaag ccgtcgtcgt tagtacgcac    720
atagttaata cccgcaccgt tttct                                           745

<210> SEQ ID NO 4
<211> LENGTH: 754
<212> TYPE: DNA
<213> ORGANISM: Unknown Organism
<220> FEATURE:
<223> OTHER INFORMATION: Description of Unknown Organism: Illustrative
      sequence data
<220> FEATURE:
<221> NAME/KEY: modified_base
<222> LOCATION: (2)
<223> OTHER INFORMATION: variable or unknown nucleotide
<220> FEATURE:
<221> NAME/KEY: modified_base
<222> LOCATION: (5)
<223> OTHER INFORMATION: variable or unknown nucleotide
<220> FEATURE:
<221> NAME/KEY: modified_base
<222> LOCATION: (14)
<223> OTHER INFORMATION: variable or unknown nucleotide
<220> FEATURE:
<221> NAME/KEY: modified_base
<222> LOCATION: (47)
<223> OTHER INFORMATION: variable or unknown nucleotide
<220> FEATURE:
<221> NAME/KEY: modified_base
<222> LOCATION: (59)
<223> OTHER INFORMATION: variable or unknown nucleotide

<400> SEQUENCE: 4
gncgntctag aggnctgacg ttgaccgtct tcgctgccga cagagantca ccgacaganc     60
tctgcggcgc gtccatgttg taggcggtgt agtccgtctg cgcaccacgg gtggtctggg    120
```

-continued

```
aaccactacc catcgcaata ctgtttgcat gatttgcact cgcgttgcta ccgatagcaa    180
taccgttgat tgcatcagtt aacaccagag tgttcaggcc aataccgatc cctgcatcac    240
cattaacaat ggttttcgca cccattgcca gcgagtcttc accgacagcc agtgaatctt    300
cttccgttga attagcatgg aagtatttgg acggtgtcgt tgctacagca ccaatcgcat    360
tctgcaattg acgaaccgta acggcgtcat gggcttcgga accatcggct acgttgatga    420
tttgacgata tttaccgtca tcaccgatag acaatgcacc gagcagttcg ccatccgtgg    480
tgtcgtaacc aataacaacg ccattttccg ttatgctggt gtcacgggag cctttggcaa    540
tcactcggct ggaaacagag ctgctaccca gggcgatacc cgtatcaacg tcgctgtagc    600
tgccctgacc aatagctacg ctgctatcgc ctttggcgac agagttataa cctatagctg    660
tagcgccaac accctgtgcg ctggcgtcgt ttgaacgcta agccgtcgtc gtaagtacgc    720
acatagttaa tacccgcacc gttttcttga atat                                754

<210> SEQ ID NO 5
<211> LENGTH: 755
<212> TYPE: DNA
<213> ORGANISM: Unknown Organism
<220> FEATURE:
<223> OTHER INFORMATION: Description of Unknown Organism: Illustrative
      sequence data
<220> FEATURE:
<221> NAME/KEY: modified_base
<222> LOCATION: (4)
<223> OTHER INFORMATION: variable or unknown nucleotide
<220> FEATURE:
<221> NAME/KEY: modified_base
<222> LOCATION: (10)
<223> OTHER INFORMATION: variable or unknown nucleotide

<400> SEQUENCE: 5
cggncggggn cctctagagt cgactgcagg catgcaagct tggcgtaacc atggtcatag     60
ctgtttcctg tgtgaaattg ttatccgctc acaattccac acaacatacg agccggaagc    120
ataaagtgta aagcctgggg tgcctaatga gtgagctaac tcacattaat tgcgttgcgc    180
tcactgcccg ctttccagtc gggaaacctg tcgtgccagc tgcattaatg aatcggccaa    240
cgcgcgggga gaggcggttt gcgtattggg cgctcttccg cttcctcgct cactgactcg    300
ctgcgctcgg tcgttcggct gcggcgagcg gtatcagctc actcaaaggc ggtaatacgg    360
ttatccacag aatcagggga taacgcagga agaacatgt gagcaaaagg ccagcaaaag    420
gccaggaacc gtaaaaaggc cgcgttgctg gcgtttttcc ataggctccg ccccctgac     480 gagcatcaca aaaatcgacg ctcaagtcag aggtggcgaa acccgacagg actataaaga    540
taccaggcgt ttccccctgg aagctccctc gtgcgctctc ctgttccgac cctgccgctt    600
accggatacc tgtccgcctt tctcccttcg ggaagcgtgg cgctttctca tagctcacgc    660
tgtaggtatc tcagttcggt gtaggtcgtt cgctccaagc tgggctgtgt gcacgaaccc    720
ccccgttcag cccgaccgct cgccttatc cggta                                755
```

METHODS, COMPOSITIONS, AND KITS FOR AMPLIFYING AND SEQUENCING POLYNUCLEOTIDES

1. CROSS-REFERENCE TO RELATED APPLICATION

This application is a Continuation of patent application Ser. No. 11/044,236, filed Jan. 26, 2005, abandoned, which claims benefit under 35 U.S.C. §119(e) to application Ser. No. 60/539,465, entitled "Methods, Compositions, and Kits for Amplifying and Sequencing Polynucleotides," filed Jan. 26, 2004, each of which is incorporated herein by reference in its entirety.

2. FIELD

The present disclosure relates to the field of molecular biology, and in particular, provides methods, compositions and kits for amplifying and sequencing polynucleotides.

3. INTRODUCTION

Polynucleotide amplification and sequencing are fundamental technologies in molecular biology and life sciences in general. A number of methods have been developed for amplification of polynucleotides. These include the polymerase chain reaction (PCR), ligase chain reaction (LCR), self-sustained sequence replication (3SR), polynucleotide sequence based amplification (NASBA), strand displacement amplification (SDA), amplification with Qβ replicase (Birkenmeyer and Mushahwar, J. Virological Methods, 35:117-126 (1991); Landegren, Trends Genetics 9:199-202 (1993)), and multiple strand displacement amplification (MSDA) (U.S. Pat. No. 6,280,949). Polynucleotide amplification procedures routinely are conducted in aqueous solution. The amplification product can be viscous and difficult to accurately pipette. In order to carry out subsequent analyses, such as sequencing, the product of the amplification reaction can be subjected to manipulative procedures such as liquid transfer, dilution, centrifugation, purification, filtration and addition of enzymes and other reagents.

DNA sequencing involves the generation of four populations of single-stranded DNA fragments, having one defined terminus and one variable terminus The variable terminus terminates at a specific given nucleotide base (either guanine (G), adenine (A), thymine (T), or cytosine (C)). The four different sets of fragments are each separated on the basis of their length, such as on a high resolution polyacrylamide gel; each band on the gel corresponds colinearly to a specific nucleotide in the DNA sequence, thus identifying the positions in the sequence of the given nucleotide base. One method of DNA sequencing is dideoxy sequencing, and involves the enzymatic synthesis of a DNA strand. Typically, four separate syntheses are run, each reaction being caused to terminate at a specific base (G, A, T or C) via incorporation of the appropriate chain terminating dideoxynucleotide. Dideoxy sequencing (Sanger et al., 1997, Proc. Nat. Acad. Sci. 74:5463) requires a single-stranded template to which the primer can anneal. Single-stranded templates can be easily generated using specialized cloning vectors such as YAC, cosmids, plasmids and M13 vectors (Sambrook et al., 1989, Molecular Cloning: A Laboratory Manual, Cold Spring Harbor Laboratory Press; and Ausubel et al., eds., 1996, Current Protocols in Molecular Biology, John Wiley & Sons, pp. 7.1.2-7.1.6). Dideoxy sequencing can also be readily carried out using double-stranded DNA if it is first denatured with alkali or heat.

Automated robotic systems are available for high-throughput sample processing. However, each additional manipulative step slows down the overall analysis, increases the risk of contamination and increases the risk of contamination. There is a need for methods and compositions that eliminate fluid transfer steps and other manipulations that are commonly required in proceeding from amplification to sequencing.

4. SUMMARY

In a general aspect, the present teachings concerns methods, compositions, and kits useful for amplifying and sequencing at least a region of a polynucleotide. The method includes an amplification step and a sequencing step. These steps can be carried out in the same reaction vessel or well, thus avoiding liquid transfers and other sample manipulations.

In some embodiments, the method includes incubating a target polynucleotide with a composition comprising an amplification primer, a processive amplification polymerase, a sequencing primer, a sequencing polymerase, deoxynucleoside triphosphates suitable for template-dependent primer extension, and a terminating nucleotide. The incubation can be carried out at a first temperature which can be suitable for amplifying the nucleic acid with the processive amplification polymerase. The amplification product of the incubation at the first temperature can be incubated at a second temperature which can be suitable for forming a plurality of differently-sized extended sequencing primers with the sequencing polymerase. Thus, a temperature switch can be used to alter the annealing conditions of the incubation. In some embodiments, the incubations at the first and second temperatures are repeated in four separate incubations in the presence of a terminating nucleotide suitable for terminating primer extension at A, C, G/I, or T/U, respectively. The sequencing primer can be labeled with a detectable label. In some embodiments, the incubations at the first and second temperatures include four different terminating nucleotides, each of which terminates template-dependent primer extension at a different template nucleotide. Each of the four different terminating nucleotide can be labeled with a different, distinguishable label.

In a general feature of the above methods, the second temperature can be selected such that the amplification primer does not substantially hybridize to the amplification products generated at the first temperature, but only the sequencing primer substantially hybridizes to these amplification products. At the second temperature, extension from the sequencing primer can be initiated at the site where the sequencing primer anneals and continues until termination occurs by incorporation of a terminating nucleotide that will not support continued DNA elongation. In some embodiments, a plurality of amplification primers can be used during the incubation at the first temperature. The amplification primer(s), and sequencing primer, are typically designed such that the $T_m$ value of the amplification primer(s) is(are) lower than the $T_m$ value of the sequencing primer under the selected reaction conditions.

The method can be performed using a target polynucleotide obtained by an isolation technique. Alternatively, the method can be performed directly on a sample, such as a colony or plaque sample, or an aliquot of liquid medium containing a bacterial colony or culture.

Extended sequencing primers can be evaluated to determine their sequence using various standard techniques including size separation and detection methods.

Other aspects disclosed herein involve compositions for use in amplifying and sequencing a polynucleotide. In some embodiments, a composition includes at least one amplification primer and a sequencing primer. In some embodiments, a composition includes a processive polymerase and a sequencing polymerase. In some embodiments, a composition can include one or more of the following: deoxynucleoside triphosphates suitable for template-dependent primer extension, and at least one terminating nucleotide.

Another aspect concerns kits that can be used to carrying out the method. In some embodiments, the kits can include the following: at least one amplification primer; a sequencing primer; deoxynucleoside triphosphates suitable for template-dependent primer extension; at least one terminating nucleotide; a processive polymerase; a sequencing polymerase; one or more reagents; and instructions for carrying out the method.

The novel methods, compositions and kits provided herein are based in part on the surprising discovery by Applicants that terminating nucleotides used conventionally in polynucleotide sequencing do not substantially interfere with the amplification by processive polymerases. The amplification reaction can be carried out in the presence of reagents required for a subsequent sequencing reaction, which can be performed at an elevated temperature, thereby eliminating the need to provide separate reaction mixtures and/or vessels for carrying out both polynucleotide amplification and sequencing reactions.

The method, compositions, and kits can be used in a wide variety of applications such as genetic studies, forensics and diagnostics. These and other features of the present teachings are set fourth below.

5. BRIEF DESCRIPTION OF THE DRAWINGS

The skilled artisan will understand that the drawings, described below, are for illustration purposes only. The drawings are not intended to limit the scope of the present teachings in any way.

Figure 1:
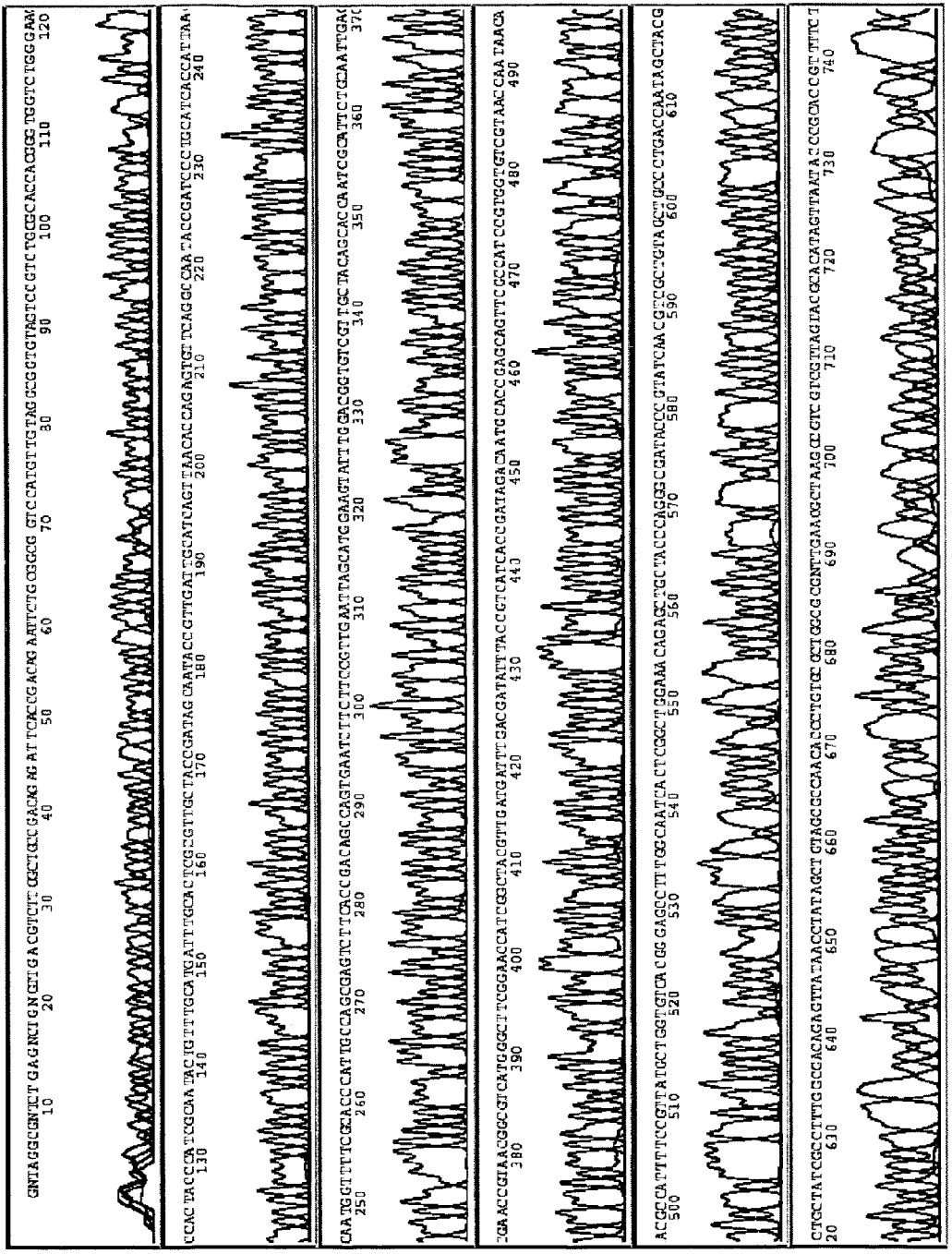
FIG. 1 illustrates sequencing data obtained in which an amplification and sequencing method was performed directly on a bacterial culture sample.

6. DESCRIPTION OF THE VARIOUS EMBODIMENTS 6.1 Definitions

Unless stated otherwise, the following terms and phrases as used herein are intended to have the following meanings:

The term "label" refers to a moiety that, when attached to compounds such as nucleotides and/or polynucleotides, render such compounds detectable using known detection means, e.g., spectroscopic, photochemical, radioactive, biochemical, immunochemical, enzymatic or chemical means. Exemplary labels include but are not limited to fluorophores, chromophores, radioisotopes, spin labels, enzyme labels, infrared labels, and chemiluminescent labels. Examples, of useful labels can include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. Colloidal gold label can be detected by measuring scattered light. In addition, such labels include components of multi-component labeling schemes, e.g., a system in which a ligand binds specifically and with high affinity to a detectable anti-ligand, e.g., a labeled antibody binds to its corresponding antigen. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

"Direct labels" are detectable labels that are directly incorporated into the polynucleotide during sequencing. So called "indirect labels" are joined to polynucleotide after the sequencing reaction. An indirect label can be attached to a binding moiety that has been attached to the elongated sequencing primer. Thus, for example, the sequencing primer can be biotinylated. After the sequencing reaction, an avidenconjugated fluorophore will bind the biotin bearing elongated primer providing a label that can be easily detected. For a detailed review of methods of labeling polynucleotides and detecting labeled polynucleotides see Laboratory Techniques in Biochemistry and Molecular Biology, Vol. 24: Hybridization With Nucleic Acid Probes, P. Tijssen, ed. Elsevier, N.Y., (1993).

The term "nucleoside" refers to a compound consisting of a purine, deazapurine, or pyrimidine nucleoside base, e.g., adenine, guanine, cytosine, uracil, thymine, 7-deazaadenine, 7-deazaguanosine, that can be linked to the anomeric carbon of a pentose sugar, such a ribose, 2'-deoxyribose, or a 2',3'-di-deoxyribose. When the nucleoside base is purine or 7-deazapurine, the pentose is attached at the 9-position of the purine or deazapurine, and when the nucleoside base is pyrimidine, the pentose is attached at the 1-position of the pyrimidine. The term "nucleotide" as used herein refers to a phosphate ester of a nucleoside, e.g., a mono-, a di-, or a triphosphate ester, wherein the most common site of esterification is the hydroxyl group attached to the C-5 position of the pentose. "Nucleotide 5'-triphosphate" refers to a nucleotide with a triphosphate ester group at the 5' position.

The term "polynucleotide" means polymers of nucleotide monomers including double and single stranded deoxyribonucleotides, ribonucleotides, α-anomeric forms thereof, and the like. Monomers are linked by "internucleotide linkages," e.g., phosphodiester linkages, where as used herein, the term "phosphodiester linkage" refers to a phosphodiester bond. Whenever a polynucleotide is represented by a sequence of letters, such as "ATGCITG," it will be understood that the nucleotides are in 5' to 3' order from left to right.

"Template" as used herein refers to a polynucleotide, such as DNA or RNA, which can be capable of serving as a substrate for the synthesis of a complementary polynucleotide strand. Polynucleotide templates can be in a double-stranded or single-stranded form. However, if the template is double-stranded at the start of a reaction it can first be treated to denature the two strands into a single-stranded, or partially single-stranded, form. Methods are known to render double-stranded polynucleotides into single-stranded, or partially single-stranded, forms, such as heating, or by heating to about 90°-100° C. for about 1 to 10 minutes, or by alkali treatment, such as a pH greater than 12.

As used herein, the term "primer" refers to a polynucleotide that possesses a free 3'-OH group which upon apposition to a polynucleotide template is recessed relative to the 5' end of the template and thus is capable of acting as a site of initiation of the synthesis or polymerization of a polynucleotide having a sequence that is complementary to the sequence of the template strand.

"Primer extension" is the enzymatic addition, i.e. polymerization, of monomeric nucleotide units to a primer while the primer is hybridized (annealed) to a template polynucleotide. Primer extension can be initiated at the template site where a primer anneals. One or more different nucleotide 5'-triphosphates can be present in the reaction mixture such that the complementary nucleotide is incorporated by a polymerase enzyme according the template sequence. Extension continues until nucleotides are depleted, the enzyme is no longer functional, or termination occurs by incorporation of a terminating nucleotide that will not support continued DNA elongation. Chain-terminating nucleotides are typically 2',3'-dideoxynucleotide 5'-triphosphates (ddNTP), which lack the 3'-OH group necessary for 3' to 5' DNA chain elongation. Other terminating nucleotides include 2',3'-dideoxy-dehydro; 2'-acetyl; 2'-deoxy, halo; and other 2'-substituted nucleotide 5'-triphosphates as further described hereinbelow.

6.2 Method

In one aspect, provided herein a method of amplifying and sequencing a polynucleotide. In some embodiments, the method comprises amplifying at least a region of a target polynucleotide with an amplification polymerase and one or more amplification primers at a first temperature in the presence of a sequencing primer, a sequencing polymerase, deoxynucleoside triphosphates suitable for template-dependent primer extension, and at least one terminating nucleotide. The amplification can be carried out at a first temperature suitable for hybridization between the amplification primer and a strand of the target polynucleotide. The target polynucleotide acts as an "amplification template." After a selected period of time, the temperature can be elevated to a second temperature. At the second temperature, the products of the amplification are used as a "sequencing template" to which the sequencing primer hybridizes, and a plurality of differently-sized extended sequencing primers can be formed. The amplification polymerase can be a processive polymerase. In some embodiments of the method, four different reactions are carried out with a different terminating nucleotide in each reaction. In some embodiments, a single reaction can be carried out in the presence of a plurality of different terminating nucleotides. In some embodiments, four different terminating nucleotides are present and each can be labeled with a different spectrally resolvable label. The method can include separating the differently sized extended sequencing primers based on their sizes, detecting the label on the extended sequencing primers, and determining therefrom a sequence of the polynucleotide.

The sequences and lengths of the amplification primer(s), and of the sequencing primer, are designed to give $T_m$ values that are suitable for priming amplification in accordance with the method. "$T_m$" as used herein, refers to the melting temperature (temperature at which one-half of the base pairs in a duplex have dissociated) of the duplex between a primer and its template. The melting temperature for the hybridization of an amplification primer to the amplification template is referred to herein as "$T_{m,a}$" and the melting temperature for the hybridization of the sequencing primer to the sequencing template "$T_{m,s}$". All temperatures are understood to be in degrees Centigrade (° C.) when not specified. $T_m$ can be empirically determined or can be calculated, e.g., using the nearest-neighbor thermodynamic values of Breslauer et al., (1986, Proc. Natl. Acad. Sci. USA 83:3746-3750) for DNA and Freier et al., (1986, Proc. Natl. Acad. Sci. USA 83:9373-9377) for RNA.

The empirical determination of $T_m$ can be accomplished using several standard procedures, based on ultraviolet hypochromism, for example, by monitoring the spectrum at 260 nm (e.g. as described in Biochemistry—The Molecular Basis of Cell Structure and Function, 2nd Edition, Lehninger, Worth Publishers, Inc., 1970, pp. 876-7). The various methods of determining $T_m$ values can produce slightly differing values for the same DNA molecule, but those values should not vary from each other by more than about 2° C. or 3° C.

In some embodiments, the $T_m$ values can be calculated using the formula (I):

$$T_m(° C.)=67.5+0.34(\%[G+C])-395/N \qquad (I)$$

wherein "G" and "C" represent the number of guanine and cytosine nucleotides, respectively, and "N" represents the total number of nucleotides in the primer. $T_m$ values obtained by this calculation correlate very well with the values determined empirically at room temperature using conventional UV hypochromism and a conventional diode array spectrophotometer (scanning rate of about +1° C./min) for a solution of primer in 10 mmolar tris(hydroxymethyl)aminomethane buffer (pH 8.5) having an ionic strength of at least about 60 mmolar provided by one or more inorganic or organic salts, such as magnesium chloride, magnesium sulfate, potassium chloride, sodium chloride, and others readily apparent to one skilled in the art. The amount of primer and its complement in the solution used to determine formula I are sufficient to provide an optical density of from about 0.5 to about 1.0 OD units.

An "annealing temperature" is defined herein to include the range of from about 1-2° C. above the melting temperature of a primer to about 5-10° C. below such temperature. Guidance for selecting appropriate primers given design constraints as indicated herein and the nature of the polynucleotide targets can be found in many references, including Rychlik et al., 1989, Nucl. Acids. Res. 17:8453-8551; Lowe et al., 1990, Nucl. Acids Res. 18:1757-1761, Hiller et al., 1991, PCR Methods and Applications 1:124-128; Wetmur, 1991, Critical Reviews in Biochemistry and Molecular Biology, 26:227-259; Breslauer et al., 1986, Proc. Natl. Acad. Sci. 83: 3746-3750; Innis et al, editors, 1990, PCR Protocols (Academic Press, New York); and the like.

In some embodiments of the method, the first temperature typically will be lower than the second temperature. At the second temperature, extension from the sequencing primer can be initiated at the site where the sequencing primer anneals and continues until termination occurs by incorporation of a terminating nucleotide. Priming by the amplification primer(s) at the second temperature could generate products that interfere with subsequent analysis. The difference between the $T_{m,a}$ and $T_{m,s}$ values, and the respective annealing temperatures, can be selected to equal or exceed a minimum or threshold value in order to substantially avoid this possible interference. In some embodiments, the difference in annealing temperatures can be about 5° C. In some embodiments, the difference in annealing temperatures can be a value in the range of about 5° C. to about 60° C. In some embodiments, the annealing temperature of the amplification primer can be at least 10° C., at least 20° C., at least 30° C. and at least 50° C. lower than the annealing temperature of the sequencing primer.

In some embodiments of the method, the first temperature can be maintained at the annealing temperature of duplex(es) formed between the target polynucleotide and the amplification primer(s) and the second temperature can be maintained at the annealing temperature of the duplex between the sequencing primer and the product of the amplification step. For example, the first temperature can be in the range of about 20° C. to about 70° C. and the second temperature can be in the range of about 35° C. to about 80° C. The temperatures selected will depend, in part, on the amplification polymerase and on the sequencing polymerase used as further described hereinbelow.

The reaction conditions at the first and second temperatures can include an appropriate buffering system to maintain a constant pH, divalent and monovalent cations (such as $MgCl_2$ and KCl), and can include reducing agents and detergents that can be added to enhance the reaction rate, fidelity, or other parameters.

The duration of the amplification at the first temperature will depend, in part, upon the length of the target polynucleotide and upon the amount of amplification desired. The amplification can last from about 1 hr to 24 hr, for example. Representative reaction conditions for isothermal amplifications are exemplified herein and in U.S. Pat. No. 6,124,120. The duration of the reaction at the second temperature will depend in part upon the sequencing polymerase selected. Representative reactions for conventional sequencing reactions are exemplified in Ansorge, W., Voss, H., and Zimmermann. J., eds., 1996, *DNA Sequencing Strategies*, Wiley-Liss; and Sambrook, et al., 1986. In carrying out the methods, reaction conditions are typically selected such that the buffer system and other reagents for the first step are compatible with the conditions required for the second step.

The concentration of the amplification polymerase and sequencing polymerase are not critical as long as they are present in sufficient amount to function adequately in the method. In some embodiments, the amount of amplification polymerase and sequencing polymerase present in the incubation can range from about 0.01 units/μl to about 10 units/μl for each. Suitable concentrations for the amplification primer(s) and for the sequencing primers can be determined by performing reactions at various concentrations of these primers. In some embodiments, the total concentration of amplification primers in the reaction mixture can range from about 0.05 μM to about 10 mM and the primers can be present in equimolar concentrations. In some embodiments, the concentration of the sequencing primer can range from about 0.05 μM to about 50 μM. In some embodiments, the sequencing primer can be present at a mole ratio of less than about 10% as compared to the total amplification primers. In some embodiments, the sequencing primer can be present at a mole ratio of less than about 1% as compared to the total amplification primers. The sequencing primer to sequencing template ratio can be 1:1 for a single-stranded template. The concentration of each deoxyribonucleotide triphosphate can be in the range of about 1 μM to about 10 mM at the start of the amplification. When the method is carried in the present of four terminating nucleotides, they can be present at a concentration in the range of about 10 nM each to about 100 μM each. When the method uses a single terminating nucleotide in four separate incubations, the concentration of terminating nucleotide can be in the range of about 10 nM to about 100 μM. The template can be present at any suitable concentration, e.g., in the range of about 1 ng/μl to about 10 μg/μl.

In some embodiments of the methods, the amplification step and/or the sequencing step can be cycled through two or more temperatures. In one example, an amplification carried out in the presence of exo(−)Bst DNA polymerase included 50 cycles of a thermal sequence including 15 seconds at 48° C., followed by 15 seconds at 50° C. The instant methods can be used in conjunction with conventional thermal cycling sequencing reactions (e.g. see Ausubel et al., 1996, Chapter 7). For example, the sequencing reaction can be cycled through temperatures (e.g. 20 seconds at 95° C., 20 seconds at 55° C., 20 seconds at 72° C.) for a selected number of cycles (e.g. 20 cycles). In this embodiment, the cycling temperatures are all above the annealing temperature for the amplification primer(s). In another example, a sequencing step was carried out for 25 cycles of the following thermal sequence: 95° C., 10 seconds; 50° C., 5 seconds; 60° C., 4 minutes.

In the practice of the present teachings, the reaction temperature can be maintained at selected values during the amplification reaction and during the sequencing reaction. Any conventional temperature control system can be used for this purpose. An example of a suitable system is the ABI Prism® 7700 Instrument (Applied Biosystems, an Applera Corporation business).

The products of the sequencing reaction can be analyzed by a wide variety of methods. For example, the products can be separated by a size-dependent process, e.g., gel electrophoresis, capillary electrophoresis or chromatography; and the separated fragments detected, e.g., by laser-induced fluorescence (see, e.g., U.S. Pat. Nos. 5,945,526; 5,863,727; 5,821,058; 5,800,996; and 5,332,666). In some embodiments, the product of the sequencing reaction can analyzed by use of gel electrophoresis and visualized using stains such as ethidium bromide or silver stain. The sequencing reaction products can also be analyzed by mass spectrometric methods (see, e.g., U.S. Pat. Nos. 6,225,450 and 5,210,412).

6.3 Polynucleotide Samples

A target polynucleotide for use with the methods and compositions can be derived from any living, or once living, organism, including but not limited to prokaryote, eukaryote, plant, animal, and virus. The polynucleotide can originate from a nucleus of a cell, e.g., genomic DNA, or can be extranuclear polynucleotide, e.g., plasmid, mitochondrial polynucleotide, various RNAs, and the like. The polynucleotide sequence can be first reverse-transcribed into cDNA if the target polynucleotide is RNA. Furthermore, the target polynucleotide sequence can be present in a double stranded or single stranded form. The target polynucleotide can be essentially any natural or synthetic polynucleotide, can be single stranded or double stranded, linear or circular. Other non-limiting examples of polynucleotides include chromosomal or genomic DNA, cloned DNA, the product of a PCR or other amplification, p1 vectors, viral genomes, ligation products, cosmid DNA, YAC, BAC, and MAC.

A variety of methods are available for obtaining a polynucleotide for use with the disclosed methods and compositions. When the polynucleotide sequence is obtained through isolation from a biological matrix, isolation techniques can include (1) organic extraction followed by ethanol precipitation, e.g., using a phenol/chloroform organic reagent (e.g., Ausubel et al., eds., Current Protocols in Molecular Biology Volume 1, Chapter 2, Section I, John Wiley & Sons, New York (1993)), such as by using an automated DNA extractor, e.g., the Model 341 DNA Extractor available from PE Applied Biosystems, an Applera Corporation (Foster City, Calif.); (2) stationary phase adsorption methods (e.g., Boom et al., U.S. Pat. No. 5,234,809; Walsh et al., 1991, Biotechniques 10:506-113); and (3) salt-induced DNA precipitation methods (e.g., Miller et al., 1988, Nucl. Acids Res. 16:9-10), such precipitation methods being typically referred to as "salting-out" methods. Each of the above isolation methods can be preceded by an enzyme digestion step to help eliminate unwanted protein from the sample, e.g., digestion with proteinase K, or other like proteases.

In some embodiments, no isolation techniques are used, and amplification can be performed directly on a sample (e.g., directly on a colony or plaque sample, an aliquot of liquid medium containing a bacterial colony or culture, or an aliquot from a bacterial glycerol stock).

6.4 Amplification Polymerase

Another aspect of the disclosure concerns DNA polymerases used for polynucleotide amplification. The polymerase used in the amplification can be a processive polymerase. In addition, the polymerase used in amplification can exhibit strand displacement activity and/or proofreading activity. In some embodiments, the amplification step can be carried out isothermally.

By processive is meant that the DNA polymerase is able to continuously incorporate nucleotides using the same primer, for a substantial length without dissociating from either or both the primer or the template molecules, under the amplification reaction conditions. In some embodiments, processive polymerases used herein will remain bound to the template during the extension of up to at least 50 nucleotides to about 1.5 kilobases, up to at least about 1 to about 2 kilobases, and in some embodiments at least 5 kb-10 kb, during the amplification reaction.

In some embodiments, DNA polymerases used in amplification of the target polynucleotide are capable of displacing, either alone or in combination with a compatible strand displacement factor, a hybridized strand encountered during replication. Such polymerases are referred to herein as strand displacement DNA polymerases. Strand displacement results in synthesis of multiple copies of a target sequence (see, e.g., U.S. Pat. No. 6,280,949).

A 5' to 3' exonuclease activity, if present, might result in the destruction of a synthesized strand. Amplification primers can include features that interfere with such activity, as described below. In some embodiments, an amplification polymerase with a reduced level of 5' to 3' exonuclease and/or a reduced level of 3'-5' exonuclease activity can be used. For some polymerases, the level of exonuclease activity can be reduced to a level which can be less than 10%, 1.0%, or less than 0.1% of the normal activity in some cases. Examples of polymerases having reduced exonuclease activity due to genetic engineering or chemical modification have been described (see, e.g., U.S. Pat. Nos. 5,198,543, 5,001,050 and 5,576,204 and Tabor et al., 1989, J. Biol. Chem. 264:6447-6458).

Non-limiting examples of suitable amplification polymerases include Bst DNA polymerase, exo(−)Bst DNA polymerase (Aliotta et al., 1996, Genet. Anal. 12:185-195), exo(−)Bca DNA polymerase (Walker and Linn, 1996, Clinical Chemistry 42:1604-1608), bacteriophage M2 DNA polymerase (Matsumoto et al., 1989, Gene 84:247), bacteriophage PRD1 DNA polymerase (Jung et al., 1987, Proc. Natl. Acad. Sci. USA 84:8287), VENT® DNA polymerase, exo(−) VENT DNA polymerase, DEEPVENT DNA polymerase, exo(−) DEEPVENT® DNA polymerase (New England Biolabs), Klenow fragment of DNA polymerase I (Jacobsen et al., 1974, Eur. J. Biochem. 45:623-627), T5 DNA polymerase (Chatterjee et al., 1991, Gene 97:13-19), Thermo Sequenase™ (Amersham Biosciences), T4 DNA polymerase holoenzyme (Kaboord and Benkovic, 1995, Curr. Biol. 5:149-157), bacteriophage Cp-1 DNA polymerase, bacteriophage φPRD1 DNA polymerase (Zhu and Ito, 1994, Biochim Biophys. Acta. 1219:267-276), bacteriophage φ29 DNA polymerase and bacteriophage φ29-type DNA polymerase (Amersham Biosciences and New England Biolabs; and see, e.g., U.S. Pat. No. 5,001,050), bacteriophage φ15 DNA polymerase, bacteriophage φ21 DNA polymerase, bacteriophage PZE DNA polymerase, bacteriophage PZA DNA polymerase, bacteriophage Nf DNA polymerase, bacteriophage M2Y DNA polymerase, bacteriophage B103 DNA polymerase, bacteriophage SF5 DNA polymerase, bacteriophage GA-1 DNA polymerase, bacteriophage Cp-5 DNA polymerase, bacteriophage Cp-7 DNA polymerase, bacteriophage PR4 DNA polymerase, bacteriophage PR5 DNA polymerase, bacteriophage PR722 DNA polymerase, bacteriophage L17 DNA polymerase, AmpliTaq® Gold DNA polymerase (Applied Biosystems, an Applera Corporation), AmpliTaq® DNA polymerase, Tth DNA polymerase (Applied Biosystems, an Applera Corporation), and mixtures thereof.

Other suitable amplification polymerases include Tbr, Tfl, Tru, Tli, Tac, Tne, Tma, Tih, Tfi, Pfu, Pwo, Kod, Bst, Sac, Sso, Poc, Pab, Mth, Pho (Transgenomic, Inc.), ES4, PRUTurbo™, AcccuType™ (Stratagene), ULTRA™, PfuUTP, PfuTurbo™, Easy-A™, Herculase™, TaqPlus® MAXX™ and mixtures thereof.

Different polymerases can have different optimal temperature, pH values, or ion concentrations. Amplification can be performed at a temperature compatible with the enzyme being used, for example, 32° C. for φ29 DNA polymerase, from 37° C. to 64° C. for exo(−) Bst DNA polymerase, or from about 60° C. to 70° C. for an enzyme from a hyperthermophylic organism. The optimum temperature can depend upon the length of the primer. For example, for φ29 DNA polymerase, an optimal temperature of about 20° C.-30° C. was observed when using hexamer primers, but an optimal temperature of about 35° C. was observed when using octamers. An optimal temperature of 50° C. was observed for exo (−) Bst DNA polymerase when using 10-mer primers.

The amplification reaction can include accessory proteins, non-limiting examples of which include BMRF1 polymerase accessory subunit, adenovirus DNA-binding protein, herpes simplex viral protein ICP8, single-stranded DNA binding proteins, phage T4 gene 32 protein, RecA, calf thymus helicase, pyrophosphatase, p3, p5 and p6 or mixtures thereof. An accessory protein can be present in a reaction at a concentration in the range of about 0.1 to 10 µg/µl.

In some embodiments, the polymerase will include strand displacement activity. "Strand displacement" as used herein refers to the phenomenon in which a chemical, physical, or biological agent, for example, a DNA polymerase, causes the dissociation of a base-paired polynucleotide from its complementary strand in a 5' to 3' direction in conjunction with, and in close proximity to, template-directed polynucleotide synthesis. Strand displacement begins at the 5' end of a base-paired polynucleotide sequence and proceeds in consequence of polynucleotide synthesis immediately 5' to the displacement site. Both the newly synthesized and displaced polynucleotides have the same base sequence, which is complementary to the template strand. DNA polymerases such as *E.*

*coli* DNA polymerase I, the Klenow fragment of DNA polymerase I, the bacteriophage T7 DNA polymerase, and the bacteriophage T5 DNA polymerase, are non-limiting examples of enzymes which possess both polymerase activity and strand displacement activity. Agents such as helicases can be used in conjunction with polymerases which do not strand displace, in order to produce the effect of strand displacement, that is, displacement of a polynucleotide strand coupled to the synthesis of a polynucleotide strand of the same sequence. For a discussion of strand displacement see Kornberg, A., DNA Replication W. H. Freeman & Co., San Francisco, Calif., 1980.

6.5 Sequencing Polymerase

Another aspect of the present disclosure concerns sequencing polymerases. The sequencing polymerase can include any polymerase that can be conventionally used for polynucleotide sequencing. Non-limiting examples of suitable sequencing polymerases include: *E. coli* DNA polymerase I, the Klenow fragment of *E. coli* DNA polymerase I, bacteriophage T5 DNA polymerase, bacteriophage T7 DNA polymerase and mixtures thereof. Another example is TaqFS® which was used at a temperature in the range of about 60° C.-70° C.

In some embodiments, the same enzyme can be used as both the amplification and the sequencing polymerase. However, the enzyme must be capable of functioning at the various temperatures used, for the amplification reaction and for the sequencing reaction. In one example, exo(–) Bst DNA polymerase was used both in an amplification at about 50° C. and during subsequent sequencing at a temperature in the range of about 60° C.-65° C.

6.6 Primers

An additional aspect of the instant disclosure concerns primers used in polynucleotide amplification and sequencing reactions. Essentially any primer can be used for these reactions so long as they function in the methods described herein. Suitable length and composition of primers will depend upon whether they are used for amplification or for sequencing as indicated hereinbelow.

Primers can be synthesized by conventional approaches, e.g. Ozaki et at, Nucleic Acids Research, 20:5205-5214 (1992); Agrawal et at, Nucleic Acids Research, 18:5419-5423 (1990); Oligonucleotide Synthesis, A Practical Approach, M. J. Gait, ed., IRL Press, Washington, 1984; or the like. The primers can be synthesized on an automated DNA synthesizer (e.g. an Applied Biosystems, an Applera Corporation) model 392 or 394 DNA/RNA Synthesizer, using standard chemistries, such as phosphoramidite chemistry, e.g. disclosed in the following references: Beaucage, et al., 1992, Tetrahedron, 48:2223-2311; U.S. Pat. Nos. 4,980,460, 4,725,677, 4,415,732, 4,458,066, and 4,973,679.

In some embodiments, the amplification primer can be designed to be resistant to 3'-5' exonuclease activity. This can be accomplished, for example, by the use of primers comprising modified internucleotide linkages (e.g., see Scheit, Nucleotide Analogs (John Wiley, New York, (1980); Englisch, Angew. Chem. Int. Ed. Engl. 30:613-29 (1991); Agrawal, Protocols for Polynucleotides and Analogs, Humana Press (1994)). Modified internucleotide linkages can be used to link nucleotides at the 3' terminus or the entire primer. Such modified internucleotide linkages can be employed provided that the hybridization efficiencies of the resulting polynucleotide and/or efficiency of the polymerases employed are still compatible with the methods described herein. Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Modified internucleotide linkages also include phosphate analogs, analogs having achiral and uncharged intersubunit linkages (e.g., Sterchak, E. P., et al., 1987, Organic Chem. 52:4202), and uncharged morpholino-based polymers having achiral intersubunit linkages (e.g., U.S. Pat. No. 5,034,506). Other analogs include 4'-α-anomeric nucleotides, 1'-α-anomeric nucleotides, and 2'-4'-linked and other "locked", bicyclic sugar modifications (i.e. locked nucleic acids (LNA) as described in WO9839352; and WO9914226). An exemplary class of polynucleotide analogs where a conventional sugar and internucleotide linkage has been replaced with a 2-aminoethylglycine amide backbone polymer can be peptide nucleic acid (PNA) (e.g., Nielsen et al., 1991, Science 254: 1497-1500; Egholm et al., 1992, J. Am. Chem. Soc. 114: 1895-1897).

In some embodiments, the 5'-terminus of primer can be modified in order to make it resistant to exonuclease. Modified internucleotide linkages at the 5' terminus can be used as described above. In some embodiments, the 5' terminal nucleotide can be blocked by covalent attachment of a blocking moiety. Essentially any blocking moiety can be used to block 5'-exonuclease as long as it does not interfere with the use of the primer in the method as disclosed herein. In some embodiments, the blocking moiety can be a detectable label. Such a label can be selected from a number of different label types including, but not limited to, fluorophores, chromophores, molecules that chemiluminesce, magnetic particles, mass markers, electron dense particles, enzymes, cofactors, electrochemically active molecules, substrates for enzymes and ligands having specific binding partners (e.g., avid/biotin). 5'-labeled primers can be prepared using conventional methods (see, e.g, U.S. Pat. Nos. 5,538,848 and 6,573,047), or can be obtained commercially.

The composition of the primer is not critical as long as it can function appropriately to prime an extension reaction in the method as disclosed herein. In some embodiments, a primer can consist solely of DNA or RNA. In some embodiments, a primer can be a chimera that includes regions of DNA, RNA, PNA and/or LNA. For example, a primer can be a DNA/RNA chimera or an LNA/DNA chimera. In a particular example, a primer can be a PNA/DNA chimera and comprising: (i) a contiguous moiety of PNA monomer units and (ii) a contiguous moiety of nucleotide monomer units with an enzymatically-extendable 3'-hydroxyl terminus. The two moieties can be covalently linked together (see, e.g., U.S. Pat. No. 6,316,230).

6.6.1 Amplification Primers

An "amplification primer" refers to a primer used in a polynucleotide amplification reaction as described herein. The sequence and length of a suitable amplification primer depends in part on the nature of the target polynucleotide to which it binds and upon the desired melting temperature. The length of an amplification primer is not critical as long as it is of sufficient length to prime the synthesis of amplification products as disclosed herein. In some embodiments, an amplification primer will range in length from about 4 to about 60 nucleotides. In some embodiments, an amplification primer ranges in length from about 4 to about 25 nucleotides.

An amplification primer can be single stranded, but can alternatively be double stranded. If double stranded, the primer can be first treated, for example, by heating at a temperature sufficient to separate the strands, before being used to prepare extension products (for example, see Nucleic Acid Hybridization, A Practical Approach, B. D. Hames and S. J. Higgins, eds., IRL Press, Washington, 1985), to about 90°-100° C. for about 1 to 10 minutes.

In some embodiments, a set of amplification primers can be used. A set of amplification primers can include any desired number of primers of different nucleotide sequence. For example, a set of primers can include a plurality of primers. A set of primers can include 3 or more primers. In some embodiments, a set of primers can include 4 or more, 5 or more, 6 or more, or 7 or more primers. In general, the more primers used, the greater the level of amplification that will be obtained. There is no fundamental upper limit to the number of primers that a set of primers can have. However, for a given target sequence, the number of primers in a set of primers will generally be limited to the number of hybridization sites available in the target sequence. For example, if the target sequence is a 10,000 nucleotide DNA molecule and 20 nucleotide primers are used, there are 500 non-overlapping 20 nucleotide sites in the target sequence. Even more primers than this could be used if overlapping sites are either desired or acceptable. In some embodiments, a set of primers can include about 300 primers, about 200 primers, about 100 primers or about 50 primers. In some embodiments, a set of primers includes from 7 to about 50 primers. Any combination of the upper and lower limits for the number of primers in a set of primers described above are specifically contemplated, including all intermediate ranges.

It is not necessary that apposition of an amplification primer to the template be at the site of a sequence identical to that of the primer. A primer which apposes to the template with some mismatch can be suitable if the mismatched primer-template hybrid can still serve as a site from which to enzymatically synthesize extension products of the primer which are complementary to the template.

In some embodiments, amplification primers are "sequence specific", i.e. are complementary to a specific sequence. A sequence specific primer can be designed to amplify a selected region within a target polynucleotide.

In some embodiments, amplification primers are random primers. By "random primers" is meant that the positions of apposition of the primers to the polynucleotide template are substantially indeterminate with respect to the polynucleotide sequence of the template under the reaction conditions used in the methods herein. Methods for estimating the frequency at which selected sequences appear in a polynucleotide are described in Volinia, S. et al., 1989, Comp. App. Biosci. 5:33-40. In some embodiments, amplification primers can have a completely random sequence (e.g., NNNNNNNNNNN; N meaning a statistically random mixture of the four bases (A, T, G, C) is used at a particular position in the primer during synthesis such that the base at that position is randomly selected). In some embodiments, the sequences of random primers may or may not be statistically random. For example, chemically synthesized random primers can be random to the extent that physical and chemical efficiencies of the synthetic procedure will allow. Random primers derived from natural sources will be less random in sequence, due to favored arrangements of bases in the source organism. Random primers prepared from naturally occurring polynucleotides can be used in the amplification methods described herein and can be prepared from naturally occurring DNA or RNA that was either homologous or heterologous to the source of the target polynucleotide. Random primers from natural DNA or RNA can be prepared by degradation of the DNA or RNA to small fragments, such as fragments of 5-50 bases or base pairs. Natural DNA or RNA can be degraded by a variety of processes, for example, enzymatically with DNase or RNase. Sets of random primers can also be purchased commercially. Non-limiting examples of suitable commercially available amplification primers include sets of random primers (e.g. as available from Ambion Inc., Amersham Pharmacia Biotech, Bio-Rad, Life Technologies, NEN™, Life Science Products Inc., New England Biolabs, Pierce Chemical Co., Promega, Roche Molecular Biomedical/Boehringer Mannhein, Stratagene, and Worthington Biochemicals, Inc.).

In some embodiments, amplification primers can include sequences that are complementary to the target polynucleotide, but can also include randomly selected bases at various positions (i.e. the primers have partially random sequences). In some embodiments, the number of positions consisting of randomly selected bases in the complementary portion of primers can be from 20% to 100% of the total number of nucleotides in the complementary portion of the primers.

The amplification primers for use in the method can comprise a set of primers having completely random sequences. In some embodiments, the set comprises the complete set of hexamers composed of bases A, G, C and T. In some embodiments, the set of primers comprises a subset of the complete set of hexamers composed of A, G, C and T. In some embodiments, the amplification primers used herein are from 8 to 30 nucleotides long and hybridize with the template polynucleotide with annealing temperatures in the range of about 20° C. to 70° C. Sets of primers having random or partially random sequences can be synthesized using standard techniques by allowing the addition of any nucleotide at each position to be randomized Primer sets can be composed of primers of similar length and/or hybridization characteristics.

An amplification primer can incorporate conventional design features. For example, an amplification primer can contain a non-complementary 5' region. For example, a primer can contain a complementary region enabling it to hybridize to the nucleic acid template, and a non-complementary region. The presence of a non-complementary region can enhance strand displacement. The 5'-terminus can be further modified as indicated above. In some embodiments, an amplification primer can include a clamp, such as a GC clamp, a PNA or an LNA clamp of 2 or more bases, at its 5' end. Primers can be designed to avoid self-complementarity and to maximize binding efficiency.

6.6.2 Sequencing Primers

Another aspect of the methods, compositions and kits concerns sequencing primers. Any conventional sequence primer can be used so long as it is compatible with the methods as described herein. Sequencing primers can be labeled to facilitate the characterization of products of the sequencing reaction. Exemplary labels include but are not limited to fluorophores, chromophores, radioisotopes, spin labels, enzyme labels and chemiluminescent labels. Certain of these labels require covalent attachment which can be accomplished using any one of a large number of known techniques employing known labels, linkages, linking groups, reagents, reaction conditions, and analysis and purification methods. When attaching a label that requires a linkage, for example, the linkage linking the label and primer should not (i) interfere with primer extension, (ii) inhibit polymerase activity or (iii) adversely affect the detectable property of the label. For example, sequencing primers can be labeled by linking a fluorogenic molecule to the 5' terminus of the primer. Guidance for selecting appropriate fluorescent labels can be found in Smith et al., 1987, Meth. Enzymol. 155:260-301, Karger et al., 1991, Nucl. Acids Res. 19:4955-4962; Haugland, 1989, Handbook of Fluorescent Probes and Research Chemicals (Molecular Probes, Inc., Eugene, Oreg.). Fluorescent labels include fluorescein and derivatives thereof (such as disclosed in U.S. Pat. Nos. 4,318,846 and 6,316,230, and by Lee et al., 1989, Cytometry 10:151-164) and 6-FAM, JOE, TAMA, ROX, HEX-1, HEX-2, ZOE, TET-1 or NAN-2, and the like. Other examples of suitable fluorophores include xanthene dyes, rhodoamine dyes, cyanine dyes, squaraine dyes and dodipy dyes. Primers can also contain reactive sites for enzymes, for example cleavage sites for restriction endonucleases or promoter sites for RNA polymerases. Such sites would allow, for example, cloning of amplification products or transcription of amplification products. Labeled primers are included in various commercially available sequencing kits (e.g. from Pharmacia Biotech; Takara Shuzo Co., Ltd.; and Visible Genetics, Inc.).

Sequencing primers for use in dideoxy sequencing (Sanger-type sequencing) are well known in the art. A "sequencing primer" can be a polynucleotide that hybridizes to a target polynucleotide to prime a sequencing reaction. The length and composition of the sequencing primer are selected such that the primer has a selected melting temperature as described herein. Exemplary sequencing primers are 10-50 nucleotides in length with 50-60% G+C. The primers can be designed to avoid formation of internal duplexes and to avoid mis-priming at other sites on the template. A sequencing primers can typically be designed to be compatible with a particular template strand. Kits are commercially available (e.g. Promega, Perkin-Elmer, Pharmacia, Stratagene, Bio-Rad, New England Biolabs, Boehringer Mannheim, ICN Biomedical) that include a cloning vector and sequencing primer that can be used in conjunction with the cloning vector. Non-limiting examples of sequencing primers include the pUC/M13 17-mer forward primer available from Promega (catalog no. Q5391) and the following primers available from Sratagene: M13 Reverse Primer (catalog no. 300304), SK 20-mer Primer (catalog no. 300305), and T3 20-mer Primer (catalog no. 300301). Non-limiting examples of suitable dideoxy sequencing vectors include M13mp19/19, M13BM20.21, BluescriptII series, pBC series, pBS, pcDNAII, PEMBL18/19, pfdA/B, pGEM9z/11z/13z f$^±$, pIBI24(−25), pSELECT1, pAM18/19, pAT153, and pTTQ (see table 7.1.1 in Ausubel et al., supra). The M13 vectors most widely used for dideoxy sequencing are a series called M13mp constructed by J. Messing et al. (Messing, et al., 1982, Gene 19:269-278). Each M13mp vector contains a unique polylinker inserted into the fifth codon of lacZ. Because the polylinker is inserted into the same site in lacZ in all M13mp derivatives, a synthetic polynucleotide—complementary to a region of lacZ just downstream on the 3' side of the polylinker—can be used as a "universal" primer for all sequencing reactions. A sequencing primer can be synthesized to include various analogs, and the ends of the sequencing primer can be protected from exonuclease activity, as described in relation to amplification primers hereinabove. A particular example of a sequencing primer suitable in some embodiments of the method is the M13 primer having the following sequence:

```
TGTAAAACGACGGCCApsGpsT       (SEQ ID NO: 1)
CAGGAAACAGCTATGApsCpsC       (SEQ ID NO: 2)
``` where "ps" represents a phosphorothioate interlinkage 6.7 Nucleoside 5'-Triphosphates In some embodiments of the method, conventional nucleotide 5'-triphosphate substrates of polymerase enzymes are present in the reaction mixture and are incorporated into the polymerization product by internucleotide phosphodiester bond formation. During primer extension, typically a mixture of nucleotide 5'-triphosphates are present, e.g. dATP, dGTP, dCTP and dTTP. In some embodiments, analogs such as dITP in place of dGTP, and dUTP in place of dTTP can be used. Nucleotide 5'-triphosphates that include base analogs can also be used during primer extension. Exemplary modified nucleoside base portions include but are not limited to 2,6-diaminopurine, hypoxanthine, pseudouridine, C-5-propyne, isocytosine, isoguanine, 2-thiopyrimidine, and other like analogs. Other nucleoside base analogs are iso-C and iso-G nucleoside base analogs (such as available from Sulfonics, Inc., Alachua, Fla. and see U.S. Pat. No. 5,432,272).

Nucleotides which terminate extendability ("terminators" or "terminating nucleotides") will typically also be present in the reaction mixture. Any conventional terminating nucleotides can be used so long as they are compatible with the methods described herein. Non-limiting examples of useful terminators include 2',3'-dideoxynucleotides (ddNTP) and 2',3'-dehydro-ddNTP. In some embodiments, the terminators are labeled with detectable labels. Individual concentrations of nucleotide 5'-triphosphates and/or terminators in the mixture can be optimized to promote the desired incorporation rates and achieve the necessary detection levels. Exemplary modified pentose portions include but are not limited to 2'-or 3'-modifications where the 2'-or 3'-position is alkoxy, e.g., methoxy, ethoxy, allyloxy, isopropoxy, butoxy, isobutoxy and phenoxy, azido, amino or alkylamino, fluoro, chloro, bromo and the like.

The nucleoside base can be linked to a fluorophore, or other detectable label, by a chemical bond or linker, the identity of which will depend upon the chemical method used to form the linker. The linker can comprise any combination of atoms that will function as a linker but will not interfere with the use of the nucleotide as described herein. A conventional linker can be used, non-limiting examples of which include alkyl groups (including substituted alky groups and alkyl groups containing heteroatom moieties), esters, amide amine, epoxy groups and ethylene groups, propyl, acetylene, and C2 alkene. In some embodiments, the linkage between the fluorophore and the nucleotide 5'-triphosphate can be an acetylenic amido or alkenic amido linkage. Linkers can also comprise alkyldiyl, aryldiyl, or one or more ethyleneoxy units. In forming the linkage, a carboxyl group on the fluorophore label can activated by forming an active ester, e.g. N-hydroxysuccinimide (NHS) ester and reacted with an amino group on the alkynylamino- or alkenylamino-derivatized nucleotide. Homo- or hetero-bifunctional linking agents are well known and can be used in forming the linker (see, e.g., 1994 Pierce Chemical Company catalog, technical section non cross-linkers, pages 155-200).

In order to facilitate detection in a multiplex assay, four different terminating nucleotide can be used, each labeled with a different fluorescent label. When a plurality of fluorescent labels are employed, they can be selected to be spectrally resolvable. As used herein, "spectrally resolvable" fluorescent labels are those with quantum yields, emission bandwidths, and emission maxima that permit separated (e.g. electrophoretically separated) polynucleotides labeled therewith to be readily detected despite substantial overlap of the concentration bands of the separated polynucleotides. Fluorescent labels include fluorescein and derivatives thereof, 6-FAM, JOE, TAMA, ROX, HEX-1, HEX-2, ZOE, TET-1 or NAN-2, and the like. Examples of suitable fluorophores include xanthene dyes, rhodoamine dyes, cyanine dyes, squaraine dyes and dodipy dyes. Fluorescent labels can include single energy transfer molecules consisting of an energy donor and acceptor dye connect by a an energy transfer linker (e.g. BigDye™ available from Applied Biosystems, an Applera Corporation). Labeled terminating nucleotides and mixtures thereof are available commercially as kits for use in sequencing (e.g. Applied Biosystems, an Applera Corporation business; Amersham Biosciences; Boehringer Mannheim; Epicentre Technologies; GENPAK Limited).

6.8 Compositions

Another aspect of the present disclosure concerns compositions useful for analyzing the base sequence of at least a regions of a target polynucleotide. In some embodiments, the composition comprises a processive polymerase and a sequencing polymerase. The composition can include at least one amplification primer and/or a sequencing primer. The composition can further include deoxynucleoside triphosphates suitable for template-dependent primer extension and can also include at least one terminating nucleotide. The sequencing primer and/or terminating nucleotide(s) can include a detectable label. The composition can also include accessory proteins to promote the amplification. In some embodiments, a composition can include a target polynucleotide, at least one amplification primer, a processive amplification polymerase, a sequencing primer, a sequencing polymerase, deoxynucleoside triphosphates suitable for template-dependent primer extension and at least one terminating nucleotide. In some embodiments, the composition can be retained at selected temperatures. For example, the composition can be retained at a first temperature suitable for amplifying the polynucleotide with the processive amplification polymerase. For example, the first temperature can be in the range from about 20° C. to about 70° C. The composition can be retained at a second temperature suitable for forming a plurality of differently-sized extended sequencing primers with the sequencing polymerase. The second temperature can be in the range from about 35° C. to about 80° C., for example.

6.9 Kits

A further aspect of the present disclosure concerns kits useful for analyzing the base sequence of a target polynucleotide molecule. In some embodiments, the kit includes a processive polymerase and a sequencing polymerase. In some embodiments, the kit includes at least one amplification primer and a sequencing primer. In some embodiments, the kit includes: a processive polymerase; a sequencing polymerase; at least one amplification primer; a sequencing primer; deoxynucleoside triphosphates suitable for template-dependent primer extension; and at least one terminating nucleotide. In some embodiments, the at least one amplification primer is capable of annealing to at least a region of the target polynucleotide at a first temperature; and the sequencing primer is capable of annealing to the amplification product obtained from the amplification of the target polynucleotide at a second temperature which is not suitable for annealing of the at least one amplification primer to said amplification product. The kit can include accessory proteins to promote the amplification and can also include buffers, salts, and co-factors. In some embodiments, the kit can include sequencing primer and/or terminating nucleotides that include detectable labels as described herein. The kit can include a control polynucleotide such as pUC18 or M13mp18 DNA. The kit can include a reverse transcriptase. In some embodiments, some of these components can be provided in a pre-mixed format. The kit can include instructions for performing the analysis. The instructions can include directions pertinent for some embodiments of the kit, such instructions describing the amplification primers and sequencing primers, the amplification and sequencing polymerases, and the appropriate first and second annealing temperatures for operation of the method. In some embodiments, the kit can include reagents for making a sequencing gel, or can include ready-made separation gel, along with dyes, reagents, and instrumentation required for running and/or analyzing the gel or column.

Unless defined otherwise, all technical and scientific terms used herein have the same meaning as commonly understood by one of ordinary skill in the art to which this disclosure belongs. Unless mentioned otherwise the techniques employed or contemplated herein are standard methodologies well known to one of ordinary skill in the art. The materials, methods and examples are illustrative only and not limiting. All numerical ranges in this specification are intended to be inclusive of their upper and lower limits Other features of the disclosure will be come apparent in the course of the following descriptions of some embodiments which are given for illustration of the disclosure and are not intended to be limiting thereof.

7. EXAMPLE

Aspects of the present teachings may further be understood in light of the following example, which should not be construed as limiting the scope of the present teachings in any way.

7.1 Example 1

Amplification and Sequencing of a 2 kb DNA Insert

This example demonstrates an embodiment of an amplification and sequencing method.

Genomic *E. Coli* DNA (catalog no. 27-4566-01, Amersham) was randomly cleaved by partial restriction enzyme digestion, and sized by agarose gel electrophoresis. Fragments ranging between 1.7 and 2 kb were extracted from the gel and ligated into a pUC19 vector, followed by transfection into *E. Coli* (MAX Efficiency® DH5α™, catalog no. 18258-012, Invitrogen).

The cells were cultured, and plated on agar. In some embodiments, a single colony was picked, and cultured overnight. In an optional rinsing technique, 10 μl of the overnight culture was transferred to a tube, spun at 2000 rpm for 10 min, inverted, and spun at 300 rpm briefly. The cell pellet was re-suspended in about 5-10 μl water. 1 μl of this re-suspension was directly subjected to amplification as described below.

In some embodiments, a single colony was picked and re-suspended in 5-10 μl water, and 1 μl was directly subjected to amplification and sequencing as indicated below.

In some embodiments, plasmid DNA was isolated at a final concentration of 1 ng/μl from an overnight culture prepared as described above.

Figure 2:
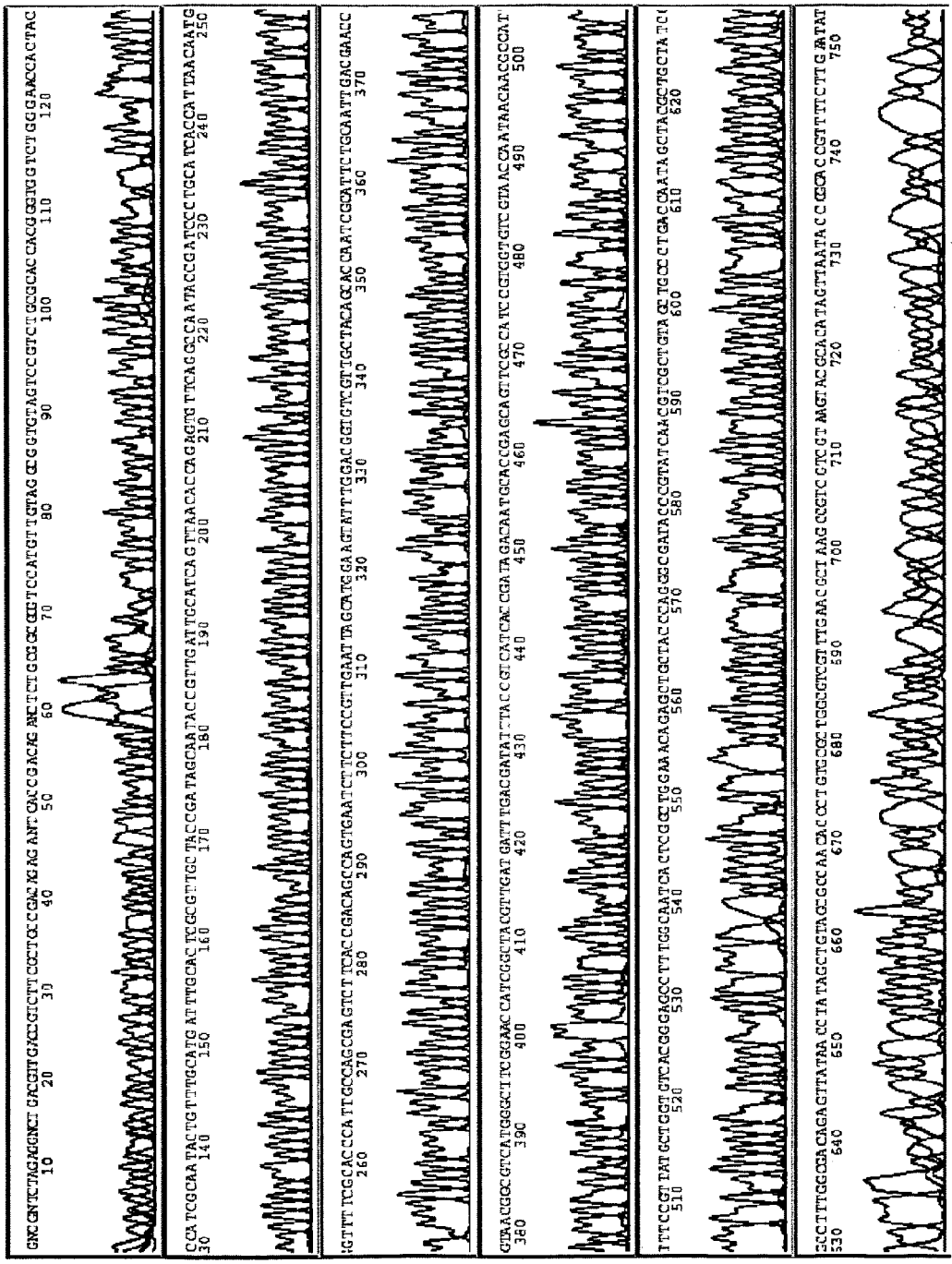
FIG. 2 illustrates sequencing data obtained in which an amplification and sequencing method was performed directly on a bacterial colony sample.
Figure 3:
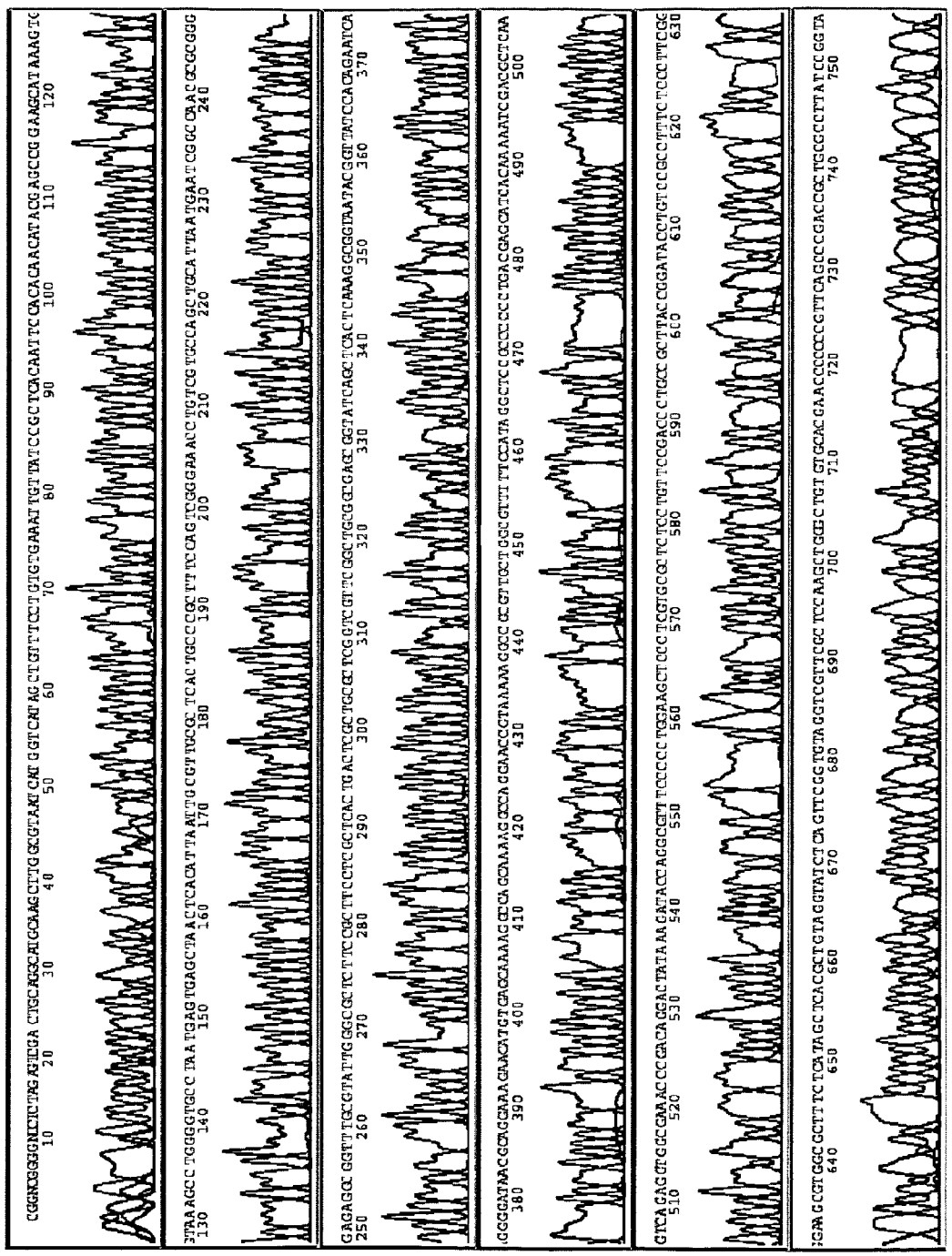
FIG. 3 illustrates sequencing data obtained in which an amplification and sequencing method was performed using plasmid DNA.

In three individual experiments (using each of the three preparations as indicated above), either 1 μl of cells from the re-suspension of an overnight culture, 1 μl of cells from the re-suspension of a colony, or 1 μl of plasmid DNA, was mixed with 150 pmole random hexamers, protected at the last two 5'-terminal bases, and incubated at 95° C. for 3 minutes. The reaction (10 μl total volume) contained the primer-template mixture, 0.05 mM dNTPs, 0.8 μl BigDye Terminator v3.1 Ready Reaction (Applied Biosystems, an Applera Corporation business, catalog no. 4337455), 1.6 μl 5× Sequencing Buffer (Applied Biosystems, an Applera Corporation business, catalog no. 4336697), 12 pmole M13 primer (SEQ ID NO:1), 0.2 μl TempliPhi Amplification Enzyme Mix (Amersham Biosciences, catalog no. 25-6400-10) and 5 mM ammonium sulfate and was incubated at 30° C. for 4 to 12 hours followed by 25 cycles of 96° C. for 10 sec, 50° C. for 5 sec and 60° C. for 4 minutes. Following the completion of cycle sequencing, the labeled sequence fragments were ethanol precipitated, dried and re-suspended in 10 μl of Hi-Di formamide (Applied Biosystems, an Applera Corporation business, catalog no. 4311320). Capillary electrophoresis was run on a 50 cm array using a model 3700 DNA analyzer (Applied Biosystems, an Applera Corporation business). The data for the overnight culture is shown in FIG. 1, for the colony sample in FIG. 2, and for the plasmid DNA in FIG. 3. The results demonstrate that amplification and sequencing can be successfully performed in a single reaction mixture.

While the foregoing has presented some embodiments of the present teachings, it is to be understood that these embodiments have been presented by way of example only. It is expected that others will perceive and practice variations which, though differing from the foregoing do not depart form the spirit and scope of the present teachings as described and claimed herein. All literature and similar materials cited in the is application, including but not limited to, patent applications, patents, and articles, books, treaties regardless of the format of such literature and similar materials, are expressly incorporated by reference in their entirety for any purpose. In the event that one or more of the incorporated literature and similar materials differ from or contradicts this application, including but not limited to defined terms, term usage, described techniques, or the like, this application controls. In this application, the use of the singular includes the plural unless specifically stated otherwise. "Comprise" and "comprises" are not intended to be limiting. The section headings used herein are for organization purposes only and are not to be construed as limiting the subject matter described in any way.

What is claimed is:

1. A method of amplifying and sequencing at least a region of a polynucleotide, said method comprising the steps of: a) incubating the polynucleotide with a composition comprising:
   at least one amplification primer;
   a processive-amplification polymerase having strand displacement activity;
   a sequencing primer;
   a sequencing polymerase;
   deoxynucleoside triphosphates suitable for template-dependent primer extension, wherein the deoxynucleoside triphosphates suitable for template-dependent primer extension are present throughout the method; and
   four different terminating nucleotides, each of which terminates template-dependent primer extension at a different template nucleotide,
   wherein a first annealing temperature of a duplex formed between the polynucleotide and the at least one amplification primer is at least 5° C. lower than a second annealing temperature of a duplex formed between the sequencing primer and an amplification product;

b) maintaining a first incubation temperature isothermally at a temperature suitable for amplifying the polynucleotide with the amplification polymerase;

c) elevating the incubation temperature to two or more temperatures suitable for forming a plurality of differently-sized extended sequencing primers with the sequencing polymerase, wherein the two or more temperatures are above the first incubation temperature; and d) determining a sequence of the polynucleotide by evaluating the plurality of differently-sized extended sequencing primers.

2. The method of claim 1 wherein each of the four different terminating nucleotides is labeled with a different, distinguishable label.

3. The method of claim 2 wherein the evaluating step comprises separating the extended sequencing primers based upon their sizes; detecting the label on the extended sequencing primers; and determining therefrom the sequence of the polynucleotide.

4. The method of claim 1 wherein the at least one amplification primer is resistant to at least one of 3' exonuclease activity and 5' exonuclease activity.

5. The method of claim 1 wherein the at least one amplification primer is a sequence specific primer.

6. The method of claim 1 wherein the at least one amplification primer is a random primer.

7. The method of claim 5 wherein the at least one amplification primer comprises a plurality of sequence specific primers.

8. The method of claim 6 wherein the at least one random amplification primer comprises a plurality of random primers.

9. The method of claim 8 wherein each of the primers comprising the plurality are of equal length and wherein the length is in the range of from 4 to 25 bases.

10. The method of claim 8 wherein each of the primers is a hexamer.

11. The method of claim 8 wherein the plurality of random primers comprises the complete set of hexamers composed of bases A, G, C and T.

12. The method of claim 11 in which the plurality of primers comprises a subset of the complete set of hexamers composed of A, G, C and T.

13. The method of claim 1 wherein the at least one amplification primer is a polynucleotide, a polynucleotide analog or a chimera thereof.

14. The method of claim 1 wherein the at least one amplification primer comprises a modified nucleoside base.

15. The method of claim 1 wherein the at least one amplification primer and/or the sequencing primer is DNA, RNA, or a chimera comprising regions of DNA, RNA, PNA, LNA, or any combination thereof.

16. The method of claim 1 wherein the sequencing primer is in the range of 10-50 bases in length.

17. The method of claim 1 wherein the sequencing primer is a polynucleotide, a polynucleotide analog or a chimera thereof.

18. The method of claim 1 wherein the four different terminating nucleoside triphosphates terminate primer extension at A, C, G/I, or T/U, each of which is labeled with a different, distinguishable label.

19. The method of claim 1, wherein the amplification polymerase and the sequencing polymerase are the same polymerase.

20. The method of claim 1, wherein the step of elevating the incubation temperature to two or more temperatures includes elevating the temperature to about 90° C. to 100° C.

21. The method of claim 1, wherein the first incubation temperature is maintained for about 1 hr to about 24 hr.

22. The method of claim 1, wherein the processive amplification polymerase is φ29 polymerase or Bst DNA polymerase.

23. The method of claim 1, wherein the processive amplification polymerase is an exo(−)Bst DNA polymerase.

24. The method of claim 1, wherein the first incubation temperature is at about the first annealing temperature.

25. The method of claim 1, wherein when the incubation temperature is elevated to the two or more temperatures, then the two or more temperatures are all above the annealing temperature for the at least one amplification primer.

* * * * *